(12) United States Patent
Kuroda

(10) Patent No.: US 8,192,748 B2
(45) Date of Patent: Jun. 5, 2012

(54) COSMETIC COMPOSITION EXHIBITING WATER-RUNABILITY, ITS MANUFACTURE AND USE

(75) Inventor: Akihiro Kuroda, Odawara (JP)

(73) Assignee: KAO Corporation, Tokyo (JP)

( * ) Notice: Subject to any disclaimer, the term of this patent is extended or adjusted under 35 U.S.C. 154(b) by 244 days.

(21) Appl. No.: 10/507,501

(22) PCT Filed: Mar. 11, 2002

(86) PCT No.: PCT/JP02/02269
§ 371 (c)(1),
(2), (4) Date: Sep. 13, 2004

(87) PCT Pub. No.: WO03/075863
PCT Pub. Date: Sep. 18, 2003

(65) Prior Publication Data
US 2005/0118121 A1    Jun. 2, 2005

(51) Int. Cl.
A61K 8/02     (2006.01)
A61K 9/16     (2006.01)
A61K 9/50     (2006.01)

(52) U.S. Cl. ........................................ 424/401; 424/490

(58) Field of Classification Search .................... 424/401
See application file for complete search history.

(56) References Cited

U.S. PATENT DOCUMENTS

| | | | | |
|---|---|---|---|---|
| 4,892,726 A | * | 1/1990 | Yonekura et al. | 424/63 |
| 6,534,044 B1 | * | 3/2003 | Wada et al. | 424/59 |
| 2003/0082218 A1 | * | 5/2003 | Ichinohe et al. | 424/401 |

FOREIGN PATENT DOCUMENTS

| | | | |
|---|---|---|---|
| EP | 05 23 911 | * | 1/1993 |
| EP | 0 590 192 A1 | | 4/1994 |
| EP | 0 987 002 A2 | | 3/2000 |
| EP | 1 213 006 A1 | | 6/2002 |
| EP | 1 291 377 A1 | | 3/2003 |
| JP | 61-65808 A | | 4/1986 |
| JP | 01211518 A | * | 8/1989 |
| JP | 5-339125 A | | 12/1993 |
| JP | 6-135817 A | | 5/1994 |
| JP | 6-135818 A | | 5/1994 |
| JP | 7-126126 A | | 5/1995 |
| JP | 7-215817 A | | 8/1995 |
| JP | 7-267819 A | | 10/1995 |
| JP | 9-12431 A | | 1/1997 |
| JP | 11-209646 A | | 3/1999 |
| JP | 2000-053554 A | | 2/2000 |
| JP | 2000-264824 A | | 9/2000 |
| JP | 2000-273010 A | | 10/2000 |
| JP | 2000-273011 A | | 10/2000 |
| JP | 2000-281525 A | | 10/2000 |
| JP | 2000309505 | * | 11/2000 |
| JP | 2000327948 A | * | 11/2000 |
| JP | 2001-152138 A | | 6/2001 |
| JP | 2001-207123 A | | 7/2001 |
| JP | 2002-114663 A | | 4/2002 |
| WO | WO 01/15658 A1 | | 3/2001 |
| WO | WO 01/36190 A1 | | 5/2001 |
| WO | WO 01/92376 A1 | | 12/2001 |

OTHER PUBLICATIONS

Fluoropolymers (Gareth Hougham Published by Springer, 1999).*

\* cited by examiner

*Primary Examiner* — Sreeni Padmanabhan
*Assistant Examiner* — Layla Soroush
(74) *Attorney, Agent, or Firm* — Foley & Lardner LLP

(57) ABSTRACT

The present invention provides a cosmetic composition comprising the following Components (A) to (E):
(A) 7 to 30% by weight of one or more kinds of non-volatile oil agents having a kinematic viscosity of 5 to 1000 $mm^2/s$ at 25° C.;
(B) 0.2 to 5% by weight of one or more kinds of water-repellent resin powders whose primary particle size is in the range of 2 to 20 μm;
(C) 0.1 to 6% by weight of one or more kinds of oil-soluble silicone resins;
(D) 20 to 60% by weight of a volatile solvent, excluding water, containing one or more kinds of volatile solvents whose boiling point at 1 atmosphere is 200° C. or lower; and
(E) 12 to 30% by weight of one or more kinds of water-repellent surface treated pigments;
and exhibiting water water-runability.
The present invention provides a cosmetic composition characterized in that the water-runability is stable without showing temperature dependency, and excellent in durability and feeling, and ultraviolet ray protective effects last for a long time.

14 Claims, No Drawings

COSMETIC COMPOSITION EXHIBITING WATER-RUNABILITY, ITS MANUFACTURE AND USE

TECHNICAL FIELD

The present invention relates to a cosmetic composition characterized by having water-runability, excellent in water-resistance, durability and touch, and ultraviolet ray protective effects which last for a long time.

BACKGROUND ART

Recently, with the aim of improving durability of sun screen, foundation, lipstick, etc., technologies of formulating water-repellent compounds and water-repellent pigments into preparations have been greatly developed. As a water-repellent compound, a fluorine compound such as perfluoropolyether, a silicone compound such as dimethylsiloxane, fluorine-modified silicone resin have been used. Furthermore, as a water-repellent pigment, a fine particle titanium oxide which has been treated with silicone or with metallic soap, etc. have been used. Since these materials have strong resistance to water or perspiration, preparations formulated with these materials exhibit properties of materials such as water-repellency.

For example, the present inventors reported in Japanese Unexamined Patent Publication No. Hei 9-12431 that a cosmetic composition superior in durability can be obtained by formulating a fluorine-modified silicone resin with excellent water and oil repellency. They also reported in Japanese Unexamined Patent Publication No. Hei 7-126126 that a cosmetic composition in which perfluoro-alkyl/polyoxyalkylene-comodified organopolysiloxane and fluoridized powder are formulated is excellent in durability. These technologies are based on the idea that "when each material is excellent in resistance to water, then the durability of the preparations is enhanced."

Meanwhile, an attempt to enhance sunburn protection performance has been continued in sun screens. They have technically taken over the above-described concept. As are shown in Japanese Unexamined Patent Publication Nos. Sho 61-65808, Hei 6-135817 and Hei 5-339125, techniques of how to formulate materials excellent in durability are centered on. It should be noted that in any of these patents, there are only such expressions as "enhance durability" and "improve lastingness."

The present inventors have conducted field tests of products in which materials capable of enhancing such durability are formulated. As a result, they have found that products whose durability was supposed to be improved are still poor in actual performance, particularly when worn in water bathing, unexpected poor durability has been confirmed. For example, with some preparations of SPF 100 level, the ultraviolet ray protective function lasted only two to three hours when worn in water. Therefore, there seemed to be a limit to coping merely by the conventional technology of enhancing the durability by combinating water-resistant materials. Particularly for use at a leisure time, a new technical approach has been required in order to impart lastingness to the preparations so as to prevent the skin from being sunburnt all day without the need to reapply the preparations once they are applied in the morning. Although foundations and eye shadow with durability for daily life have been developed, there is the problem that they easily come off in water bathing such as a swimming pool. Thus, preparations which can be used at a leisure time has been in demand. Furthermore, the water-proof test standard of US FDA is used as an indication of resistance to water. According to the test method, however, there are some cases where some products are allowed to have a sign reading that they are excellent in durability even if a person wearing them are sunburnt in the actual use. Therefore, in areas, such as Japan, where consumers have little awareness of the necessity of reapplying sunscreens, the standard fails to meet the actual situation. Accordingly, with the test results, it cannot be said that the product is excellent in durability.

DISCLOSURE OF THE INVENTION

In view of these problems, the inventors of the present invention conducted extensive studies in search of the solutions for these problems, and found that these problems can be solved by additionally imparting a performance of water-runability to preparations as a result. The technique of water-runability is comprised of a technique of forming microscopic asperities on the surface of a coating film so that it can keep an air film thereon, thereby making the contact angle between water and the coating film to 180 degree in appearance in order to eliminate interaction between the coating film and water. There are technically two ways to impart the water-runability: (1) a method of using a material having water-runability, and (2) a method of combining materials in preparations. The present invention belongs to the latter (2). Because of the water-runability of the present invention, the preparations are protected by an air barrier film. As a result, the preparations are unlikely to come off in water and long-term lastingness and durability when applied can be ensured. On the other hand, in the case of conventional water-repellent preparations, water does not uniformly fall over the coating film surface and have an interaction with the coating film, resulting in poor lastingness. The distinction between "water-repellent" and "water-runability" will be described below.

"Water repellent (hassui)" indicates a phenomenon where water is repelled. In a case where a water-repellent preparation is applied on the skin, when the coating film has any uneven spot, water in the area of a high degree of water-repellency flows down to the area of a low degree of water-repellency to form water drops, accelerating degradation of the film on the interface between the area of a high degree of water-repellency and the area of a low degree of water-repellency. When the degradation develops, it causes the coating film to yield to water and to come off. (Although it seems that the coating film repels water immediately after application, the above-described phenomenon is created very soon, and the coating film rapidly changes to get wet by water.) Conventionally, the preparations are designed to make the coating film uniform and flat to inhibit such degradation.

Meanwhile, "water-runability (kassui)" means, as the corresponding Chinese characters suggests, as "water slips," that water instantaneously flows down (slips down) the coating film. In this case, water contacts with a thin film of air, and has little contact with the coating film. Thus, the degradation of the coating film proceeds only slowly. For example, when a water-repellent coating film is formed on a glass plate, and the coating film is observed immediately after water is flowed on it, water drops are seen to form and the water films on the coating film is seen to flow down slowly. On the other hand, when a coating film with water-runability is formed on a glass plate, and the coating film is observed immediately after water is flown on it, the water on the coating film is seen to flow down rapidly. In this way, there is a distinctive difference between water-repellent and water-runability as a phenomenon. Additionally, they are different in durability as well, a product with water-runability being far better than a product with water-repellency in durability.

Moreover, the present inventors have found that the expression of water-runability may depend on water temperature, by observing the differences in appearance of water-runability when water temperature varies from 25° C. to 35° C. According to the results, it was characteristically found that the water-runability is unlikely to be exhibited at a low temperature and is more likely to be exhibited at a high temperature. Furthermore, it was also found that when the water-runability is not exhibited, the durability largely deteriorates. Therefore, the formulation and evaluation standards were reviewed, and a combination wherein the water-runability is maintained even at a lower temperature is studied to solve the problem of temperature dependency. Due to such techniques, ultraviolet ray protective effects can now be maintained all day which have conventionally been lost in a few hours, unless the applied cosmetic composition is wiped off with towels or the like.

That is, the present invention relates to a cosmetic composition comprising following Components (A) to (E):

(A) 7 to 30% by weight of one or more kinds of non-volatile oil agents having a kinematic viscosity of 5 to 1000 mm$^2$/s at 25° C.;
(B) 0.2 to 5% by weight of one or more kinds of water-repellent resin powders whose primary particle size is in the range of 2 to 20 μm;
(C) 0.1 to 6% by weight of one or more kinds of oil-soluble silicone resins;
(D) 20 to 60% by weight of a volatile solvent, excluding water, containing one or more of volatile solvents whose boiling point at 1 atmosphere is 200° C. or lower; and
(E) 12 to 30% by weight of one or more kinds of water-repellent surface treated pigments;
and having water-runability.

A second aspect of the present invention is the above-described cosmetic composition, further containing as Component (F) a highly polymerized silicone represented by the following general formula:

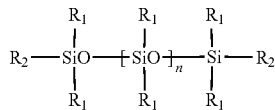

wherein $R_1$ represents a methyl group or a phenyl group; $R_2$ represents a methyl group or a hydroxyl group. Provided that the case where all of $R_1$ are phenyl groups is excluded. n represents an integer of 2,000 to 20,000.

A third aspect of the present invention is the above-described cosmetic composition containing no surfactant other than those selected from the group consisting of perfluoroalkyl-modified silicone, polyether-modified silicone, polyglyceryl-modified silicone, alkylpolyglyceryl-modified silicone and perfluoroalkyl polyether-comodified silicone.

A fourth aspect of the present invention is the above-described cosmetic composition, further containing as Component (G) one or more kinds selected from water and polyhydric alcohols.

A fifth aspect of the present invention is the above-described cosmetic composition, wherein the non-volatile oil agent contains one or more kinds selected from the group consisting of dimethylpolysiloxane, methylphenylpolysiloxane, perfluoroalkyl-modified silicone, perfluoropolyether, octyl paramethoxyciannamate, perfluoroalkyl group-containing dimethiconol and perfluoroalkyl polyether-comodified silicone.

A sixth aspect of the present invention is the above-described cosmetic composition, wherein the water-repellent resin powder is selected from an organopolysiloxane elastomer spherical powder, a silicone resin-treated organopolysiloxane elastomer spherical powder, polymethylsilsesquioxane and polyalkylsilsesquioxane.

A seventh aspect of the present invention is the above-described cosmetic composition, wherein the water-repellent resin powder is formulated in a form of being kneaded with an oil agent, finely crushed by a crusher or dispersed in water.

An eighth aspect of the present invention is the above-described cosmetic composition, wherein the oil-soluble silicone resin is one or more kinds selected from the group consisting of trimethylsiloxysiliciate, polyalkylsiloxysilicate, dimethylsiloxy unit-containing trimethylsiloxysilicate and perfluoroalkyl group-containing polyalkylsiloxysilicate.

A ninth aspect of the present invention is the above-described cosmetic composition, wherein the volatile solvent is one or more kinds selected from the group consisting of cyclic tetra- to hexamer of dimethylpolysiloxane, branched tetramer of dimethylpolysiloxane (methyltrimethicone), linear dimethylpolysiloxane and a lower alcohol.

A tenth aspect of the present invention is the above-described cosmetic composition, wherein the base of the water-repellent surface treated pigment is one or more kinds selected from the group consisting of a fine particle titanium oxide with an average primary particle size of 1 to 100 nm, a fine particle zinc oxide with an average primary particle size of 1 to 100 nm, a fine particle cerium oxide with an average primary particle size of 1 to 100 nm, an iron-doped fine particle titanium oxide with an average primary particle size of 1 to 200 nm, a fine particle silicic anhydride with an average primary particle size of 1 to 100 nm, a fine particle alumina with an average primary particle size of 1 to 100 nm and a fine particle zirconia with an average primary particle size of 1 to 100 nm.

An eleventh aspect of the present invention is the above-described cosmetic composition, wherein the surface treated pigment is coated with silica, alumina or zirconia, and further subjected to a water-repellent surface treatment.

A twelfth aspect of the present invention is the above-described cosmetic composition, wherein one or more kinds of the water-repellent surface treated pigments are formulated in a solvent or an oil agent in a mechanically ground form in advance or at the time of production of the cosmetic product.

A thirteenth aspect of the present invention is the above-described cosmetic composition, wherein the water-repellent surface treatment is selected from the treatments with organosilane, organotitanium and organoaluminum, each having an alkyl group with carbon numbers of 6 to 20 which may be substituted.

A fourteenth aspect of the present invention is the above-described cosmetic composition, wherein when 10 mg of the cosmetic composition is applied to and uniformly spread on one side of a 5×10 cm flat and smooth glass plate, and the glass plate is dried at 32° C. for 5 minutes, then repeatedly put in and out of running water at 30° C. for two minutes, then immersed completely into the water, slanted at an angle of 30 degree with respect to water surface and rapidly pulled out of the water, the cosmetic composition shows water-runability such that water drops or water films fall down from the glass surface within three seconds.

A fifteenth aspect of the present invention is the above-described cosmetic composition, wherein the coated portion has three or more of protrusion with a height of 0.2 μm or more per 10 μm-length.

A sixteenth aspect of the present invention is a method of imparting water-runability on skin or hair by applying or spraying the above-described cosmetic composition on the skin or the hair.

BEST MODE FOR CARRYING OUT THE INVENTION

As a non-volatile oil agent used in the present invention having a kinematic viscosity of 5 to 1000 mm$^2$/s at 25° C., any one may be used as long as it is used in ordinary cosmetic composition, excluding a hydrophilic non-volatile oil agent such as a polyhydric alcohol. The reason is that there is no need to set quantitative limits to hydrophilic non-volatile oil agents, since it is confirmed that water-runability can be obtained by hydrophilic non-volatile oil agents regardless of the formulation amount. As a non-volatile oil agent, an ether, an ester oil, a silicone oil, a mineral oil, a vegetable oil, a fluorochemical oil, etc. can be used. Particularly, it is effective to formulate one or more kinds selected from the group consisting of dimethylpolysiloxane, methylphenylpolysiloxane, perfluoroalkyl-modified silicone, perfluoropolyether, octyl parametoxyciannamate, perfluoroalkyl group-containing dimethiconol and perfluoroalkyl polyether-comodified silicone. It have been found that these non-volatile oil agents work effectively to provide water-runability. The ground for defining the range of 5 to 1000 mm$^2$/s at 25° C. of the present invention is that when it is less than 5 mm$^2$/s, the agent falls under the category of volatile solvents, and when it exceeds 1000 mm$^2$/S, the water-runability is lost and water-repellency is exhibited. It is preferable not to use oil agents having a kinematic viscosity exceeding 1000 mm$^2$/s (it is preferable, however, to use highly polymerized silicone to be discussed later in combination), or used in a low content so as to maintain the water-runability of the preparations as a whole. Furthermore, as the formulation amount of the non-volatile oil agent in the range of 5 to 1000 mm$^2$/s at 25° C. according to the present invention to be formulated in the cosmetic is defined 7 to 30% by weight. This is because when the oil agent is less than 7% by weight, the tendency of losing water-runability becomes greater, and when the oil agent exceeds 30% by weight, the preparations become too oily and sensualy disliked. Among the range, when the formulation amount of a non-volatile oil agent is in the range of 8 to 20% by weight is preferable, since the water-runability becomes greater and less temperature dependent. Here, the temperature dependency of the water-runability indicates that it takes time until the water-runability is exhibited, or in some cases, water-runability is not exhibited when the water temperature is low. As a result when the time that the coating film and water directly contact with each other becomes longer, there arises a problem of the durability becoming poor. If there is no temperature dependency, the water-runability is immediately exhibited and the durability is kept high.

Examples of water-repellent resin powder having a primary particle size in the range of 2 to 20 μm, used in the present invention include silicone elastomer such as an organopolysiloxane elastomer spherical powder and a silicone resin-treated organopolysiloxane elastomer spherical powder, polymethylsilsesquioxane, polyalkylsilsesquioxane, a polyfluoroethylene powder and a polypropylene powder. Among them, an organopolysiloxane elastomer spherical powder, a silicone resin-treated organopolysiloxane elastomer spherical powder, polymethylsilsesquioxane and polyalkylsilsesquioxane are preferable, and particularly a silicone elastomer is preferable. As the silicone elastomer, it is particularly preferable to select from powders having a particle form, containing particles in the range of the above-described particle size, as well as the form of the primary grain is spherical. Furthermore, it is preferable that the silicone elastomer is formulated in one or more of forms selected from being kneaded in the oil agent, or finely crushed by a crusher, or dispersed in water. The silicone elastomer may be or may not be surface treated by a different kind of a silicone compound, for example, by a silicone resin like silicone resin-treated organopolysiloxane elastomer spherical powders. Particularly preferable silicone elastomers used in the present invention include Trefil E series such as Trefil E-505, 506, 507 and 508 of Dow Corning Toray Silicone Co., Ltd. Additionally, a powder such as a spherical polyamide powder or an urethane powder which has been subjected to water-repellent surface treatment can be used. These powders may additionally be surface treated by conventionally known various surface treatments such as fluorine compound treatment, silicone resin treatment, silicone treatment, pendant treatment, silane coupling treatment, titanium coupling treatment, oil agent treatment, N-acylated lysine treatment, polyacrylic acid treatment, metallic soap treatment, amino acid treatment, plasma treatment and mechano-chemical treatment. As the amount of the water-repellent resin powder to be formulated in the cosmetic composition, the range of 0.2 to 5% by weight in terms of the mass of the resin powder can be mentioned. When the formulation amount is less than 0.2% by weight, the water-runability may become temperature dependent, and when the formulation amount exceeds 5% by weight, while water-runability can be obtained, physical strength of the coating film is reduced and when the amount of pigment is small, the durability becomes poor.

While any silicone resins used in ordinary cosmetic composition can be used as an oil soluble silicone resin to be used in the present invention, it is particularly preferable to include one or more kinds selected from the group consisting of trimethylsiloxysilicate, polyalkylsiloxysilicate, dimethylsiloxy unit-containing trimethylsiloxysilicate, and perfluoroalkyl group-containing polyalkylsiloxysilicate (trifluoropropyl-modified trimethylsiloxysilicate, etc.). As the amount of the oil soluble silicone resin to be formulated in the cosmetic composition, the range of 0.1 to 6% by weight can be mentioned. When the formulation amount is less than 0.1% by weight, the water-runability cannot be maintained, and when the amount exceeds 6% by weight, while water-runability can be obtained, there is a problem that the feeling of the cosmetic composition after application is not good. Among the above-described examples, perfluoroalkyl group-containing polyalkylsiloxysilicate is particularly effective for the cosmetic composition of the present invention. When compared with trimethylsiloxysilicate of the same mass ratio, perfluoroalkyl group-containing polyalkylsiloxysilicate was recognized to have about twice as effective as trimethylsiloxysilicate in imparting water-runability.

The volatile solvents used in the present invention include at least one kind of a volatile solvent excluding water with a boiling point of 200° C. or lower at 1 atmosphere. This is because, if the boiling point of the volatile solvent is high, the temperature for the water-runability to be exhibited becomes high, causing the water-runability to be temperature dependent. This may cause problems in durability at a low temperature. As a volatile solvent, any volatile solvents ordinary used in the cosmetic composition may be used. Examples include cyclic tetra- to hexamer of dimethylpolysiloxane, branched tetramer of dimethylpolysiloxane (methyltrimethicone), linear dimethylpolysiloxane, saturated hydrocarbon, a lower alcohol (ethyl alcohol, propyl alcohol, etc.), substitutes for flon, fluorocarbon and perfluoropolyether. Particularly, it is preferable to contain one or more kinds selected from the group consisting of tetra- to hexamer of dimethylpolysiloxane, branched tetramer of dimethylpolysiloxane, linear dimethylpolysiloxane and a lower alcohol. As the amount of the volatile solvent to be formulated in the cosmetic composition, 20 to 60% by weight can be mentioned. Although a volatile solvent usually has a tendency of lowering the water-runability, it has a large effect on the touch of the cosmetic composition. Therefore, it is necessary to formulate it in this concentration range in view of the touch adjustment effects.

In the cosmetic composition of the present invention, one or more kinds of water-repellent surface treated pigments are formulated in the ratio of 12 to 35% by weight. When the formulation amount of the water-repellent surface treated pigment is less than 12% by weight, the water-runability is likely to become temperature dependent, thus not preferable, and when the formulation amount exceeds 30% by weight, problems such as heavy touch of the cosmetic composition may occur, thus not preferable, either. Note that in the case of the water-reppellent surface treated pigment being a fine particle pigment, it is preferable to formulate in the ratio of 12 to 30% by weight. In this case, when the formulation amount exceeds 30% by weight, the surface looks whitish when the cosmetic composition is applied, or the touch of the cosmetic composition feels heavy, hence not preferable. As a pigment used in the present invention, various pigments used in cosmetic composition as a pigment can be used and any of them can be used regardless of the shape (spherical, rod-like, needle-like, plate-like, amorphous shape, scaly piece shape, spindle shape, etc.), the particle size (fume, fine particle, pigment grade, etc.) and the particle structure (porous, non-porous, etc.) and include an inorganic powder, an organic powder, a surfactant metal salt powder, a coloring pigment, a pearl pigment a metal powder pigment and a natural dye. Specifically, examples of the inorganic powders include pigment-grade titanium oxide, zirconium oxide, pigment grade zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, gold mica, crimson mica, biotite, lithia mica, silicic acid, silicic anhydride, aluminum silicate, magnesium silicate, aluminum magnesium silicate, calcium silicate, barium silicate, strontium silicate, tungstic acid metal salt, hydroxyapatite, vermiculite, higilite, bentonite, montmorillonite, hectorite, zeolite, ceramics powder, calcium secondary phosphate, alumina, aluminum hydroxide, boron nitride, silica, fine particle titanium oxide, fine particle zinc oxide and fine particle cerium oxide; the organic powders include polyamide powder, polyester powder, polyethylene powder, polypropylene powder, polystyrene powder, polyurethane powder, benzoguanamine powder, polymethyl benzoguanamine powder, polytetrafluoroethylene powder, polymethyl methacrylate powder, cellulose powder, silk powder, 12 nylon powder, nylon powder such as 6 nylon, polymethyl silsesquioxane, styrene-acrylic acid copolymer, divinylbenzene styrene copolymer, vinyl resin, urea resin, phenol resin, fluoro resin, silicon resin, acrylic resin, melamine resin, epoxy resin, polycarbonate resin, crystallite fiber powder, starch powder and lauroyl lysine; the surfactant metal salt powders (metallic soap) include zinc stearate, aluminum stearate, calcium stearate, magnesium stearate, zinc myristate, magnesium myristate, zinc cetyl phosphate, calcium cetyl phosphate and sodium zinc cetyl phosphate; the coloring pigments include inorganic red pigments such as iron oxide, iron hydroxide and iron titanate, inorganic brown pigments such as γ-iron oxide, inorganic yellow pigments such as yellow iron oxide and yellow ocher, inorganic black pigments such as black iron oxide and carbon black, inorganic purple pigments such as manganese violet and cobalt violet, inorganic green pigments such as chromium hydroxide, chromium oxide, cobalt oxide and cobalt titanate, inorganic blue pigments such as prussian blue and ultramarine, laked tar-based pigments, laked natural dyes, and synthetic resin powder in which these powders are compounded; the pearl pigments include titanium oxide-coated mica, bismuth oxychloride, titanium oxide-coated bismuth oxychloride, titanium oxide-coated talc, fish-scaly foil and titanium oxide-coated colored mica; the tar dyes include red No. 3, red No. 104, red No. 106, red No. 201, red No. 202, red No. 204, red No. 205, red No. 220, red No. 226, red No. 227, red No. 228, red No. 230, red No. 401, red No. 505, yellow No. 4, yellow No. 5, yellow No. 202, yellow No. 203, yellow No. 204, yellow No. 401, blue No. 1, blue No. 2, blue No. 201, blue No. 404, green No. 3, green No. 201, green No. 204, green No. 205, orange No. 201, orange No. 203, orange No. 204, orange No. 206, and orange No. 207; the natural dyes include powders selected from carminic acid, laccaic acid, carthamin, brazilin and crocin.

Particularly among them, it is preferable to select from a fine particle titanium oxide with an average primary particle size of 1 to 100 nm, a fine particle zinc oxide with an average primary particle size of 1 to 100 nm, a fine particle cerium oxide with an average primary particle size of 1 to 100 nm, a iron-doped fine particle titanium oxide with an average primary particle size of 1 to 200 nm, a fine particle silicic anhydride with an average primary particle size of 1 to 100 nm, a fine particle alumina with an average primary particle size of 1 to 100 nm, and a fine particle zirconia with an average primary particle size of 1 to 100 nm. In the present invention, it is necessary to carry out a water-repellent surface treatment when a pigment in an untreated stage does not float on water (having no water-repellent properties). While it is possible to formulate non-water-repellent pigments if it is a trace amount, when the amount exceeds 5% by weight based on the mass of the cosmetic composition, the water-runability may be impaired and becomes temperature dependent.

Examples of the water-repellent treatment used in the present invention may include fluorine compound treatment, silicone resin treatment, silicone treatment, pendant treatment, silane coupling treatment, titanium coupling treatment, oil agent treatment, N-acylated lysine treatment, polyacrylic acid treatment, metal soap treatment, amino acid treatment, plasma treatment and mechano-chemical treatment. Treatments by organosilane, organotitanium and organoaluminium each having an alkyl group with carbon numbers in the range of 6 to 20 which may be substituted are preferable, since pigments with higher water-repellency can be obtained. Particularly among them, silane treatment with an alkylsilane compound is preferable, and particularly among them, octylsilane treatment is preferable. Furthermore, silicone treatment is also preferable, and examples of which may include treatments with methyl hydrogenpolysiloxane (e.g., KF99P manufactured by Shin-Etsu Chemical Co., Ltd.), dimethyl group-containing methyl hydrogenpolysiloxane (e.g., KF9901 manufactured by Shin-Etsu Chemical Co., Ltd.), cyclic methyl hydrogenpolysiloxane (e.g., KF9902 manufactured by Shin-Etsu Chemical Co., Ltd.), and baking treatment therof. Furthermore, when the pigment is in the form of fine particles or has various activities such as a solid acid activity, it is preferable that the pigment is coated by one or more kinds selected from an inorganic oxide such as silica, alumina and zirconia, and further subjected to the above-described water-repellent surface treatment.

In the water-repellent surface treated pigments used in the present invention, particularly in the case of fine particle pigments, it is preferable that one or more kinds of water-repellent surface treated pigments are formulated in a solvent or an oil agent in a mechanically ground form in advance or at the time of manufacturing cosmetic composition. In this case, since secondary particles are ground, various effects such as enhancement of ultraviolet ray protective effects, lowering of whiteness, improvement in the water-runability and less problems with regard to safety caused by inhalement of powders in the manufacture of the cosmetic composition are expected. In this case, cyclic pentamer of dimethylpolysiloxane and branched tetramer of dimethylpolysiloxane are particularly preferable as a solvent.

In the present invention, in order to impart water-runability to the cosmetic composition and to reduce temperature dependency of the water-runability, it is preferable to formulate a highly polymerized silicone represented by the following general formula:

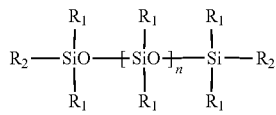

wherein $R_1$ represents a methyl group or a phenyl group; $R_2$ represents a methyl group or a hydroxy group. Provided that the case where all of $R_1$ are phenyl groups is excluded. n represents an integer of 2,000 to 20,000.)

As the above-mentioned highly polymerized silicone, besides formulating the highly polymerized silicone itself in the cosmetic composition, those which have been dissolved or dispersed in a solvent such as cyclic dimethylpolysiloxane, low viscosity dimethylpolysiloxane and liquid isoparaffin can be used. The amount of the highly polymerized silicone to be formulated in the cosmetic composition is preferably 0.1 to 6% by weight, more preferably 0.5 to 3% by weight.

In the present invention, a surfactant may be or may not be formulated in the cosmetic composition. It is preferable not to formulate surfactants other than those selected from the group consisting of perfluoroalkyl-modified silicone, polyether-modified silicone polyglyceryl-modified silicone, alkylpolyglyceryl-modified silicone and perfluoroalkyl polyether-comodified silicone. This is because while surfactants are effective in dispersing pigments, they may cause water-runability to become temperature dependent. When the dispersing properties of pigments are ensured by using water-repellent pigments (particularly a method using alkylsilane is preferable), since there is no particular need of a surfactant other than adjustment of touch, no serious problem is caused without formulating it. It has been experimentally confirmed that a surfactant, particularly if it is one of the above-mentioned silicone-base surfactants and the formulation amount in the cosmetic composition is 5% by weight or less, gives no serious influence on the water-runability.

In the present invention, it is preferable that one or more kinds selected from water and polyhydric alcohols are blended. These components have serious influence on the touch of the cosmetic composition, but no influence on water-runability. With respect to the polyhydric alcohols, tests were conducted using those of a low molecular weight such as glycerol, 1,3-butylene glycol dipropylene glycol and saccharides, to polymers such as polyethylene glycol, no influence on the water-runability was observed.

The cosmetic composition of the present invention exhibits water-runability when, after application on the skin, a slight degree of friction is applied on the coated surface by exposure to running water, or the motion of the body in water or the like. With a slight degree of friction, the surface state of the coated surface changes and an air barrier film is formed thereon, it is believed, so that the cosmetic composition is unlikely to come off by water and it becomes possible to ensure lastingness and durability for long hours. The reasons, however, are not limited to those. With the type having particularly favorable water-runability, the water-runability is exhibited within 30 seconds of exposure to running water, etc., and the properties can be maintained.

A simple method for evaluation of water-runability according to the present invention is as follows:

(1) Pretreatment: Apply 10 mg of the cosmetic composition over the entire surface of one side of a flat glass plate of 5×10 cm and uniformly spread. After drying it at 32° C. for 5 minutes, place the glass plate in and out of running water repeatedly at 25 to 35° C., particularly at 30° C. for 2 minutes. (2) water-runability test: Then completely immerse the glass plate in water and slant it at an angle of 30 degree with respect to the water surface and pull it out of the water rapidly. The water-runability is evaluated by the time of water drops or water films falling down from the glass surface. In this water-runability test, a cosmetic composition with which water drops or water films fall down the glass surface within 3 seconds is preferable, that within 1.5 seconds is more preferable. In the case of a water-repellent coating film, a lot of water drops remain on the glass plate surface, or water films are formed on the surface and a state in which water gradually recede is created. It is preferable that the application surface of a cosmetic composition of the present invention has three or more protrusions having a height of 0.2 µm or more per 10 µm-length, when a linear analysis is conducted in the vertical direction of the surface after the surface is put in water. As a method for linear analysis of the coating film, there can be mentioned methods using a non-contact three-dimensional micro surface-form measuring system, an interatomic force microscope and a laser microscope. It is preferable to use a non-contact three-dimensional micro surface-form measuring system since the coating film is soft and the asperities are fine. As a non-contact three-dimensional micro surface-form measuring system, NT-2000 manufactured by Matsushita Intertechno Co., Ltd. can be mentioned. A specific linear analysis method of the application surface form is as follows: (1) Dry the glass plate subjected to the above-mentioned pretreatment at 50° C. for 1 hour. Then, conduct linear analysis of the application surface in the vertical direction thereof by using, for example, the non-contact three-dimensional micro surface-form measuring system, to obtain the number of protrusions having a height of 0.2 µm or more with respect to the hollow portion per 10 µm-length (It is preferable to calculate the average numbers of protrusions per unit length (10 µm) by setting the analysis range of the linear analysis to 50 µm or more).

In evaluating whether the water-runability has temperature dependency, in the above-described pretreatment (1), change the temperature of the running water to 25° C., 30° C. or 35° C., and conduct a test to check water-runability at each temperature. The temperature dependency can be confirmed by observing how the water-runability changes depending on the temperature. Note that the glass plate used was one having hydrophilic properties which was washed carefully not to cause scars on the surface, confirmed that water films are formed on its surface when water is flown over the glass plate, and then dried at 50° C.

The cosmetic composition of the present invention exhibiting water-runability may use components ordinarily formulated in a cosmetic composition, other than those mentioned above, such as various ultraviolet absorbers, an oil agent, a fluorine compound, a resin, a thickener, an antimicrobial-preservative, a perfume, a moisturizing agent, a salt, a solvent, an antioxidant, a chelating agent, a neutralizing agent, a pH adjusting agent, an insect repellent and a physiologically active component. As an example of these components, there can be mentioned, for example as the ultraviolet absorber, 2-hydroxy-4-methoxybenzophenone, 2-hydroxy-4-methoxybenzophenone-5-sulfuric acid, 2,2'-dihydroxy-4-methoxybenzophenone, p-methoxyhydrocinnamic acid diethanolamine salt, para-aminobenzoic acid (hereinafter abbreviated to PABA), ethyl dihydroxypropyl PABA, glyceryl PABA, homomenthyl salicylate, methyl-O-aminobenzoate, 2-ethylhexyl-2-cyano-3,3-diphenyl acrylate, octyl dimethyl PABA, octyl salicylate, 2-phenyl-benzimidazole-5-sulfuric acid, triethanolamine salicylate, 3-(4-methylbenzylidene)camphor, 2,4-dihydroxybenzophenone, 2,2',4,4'-tetrahydroxybenzophenone, 2,2'-dihydroxy-4,4'-dimethoxybenzophenone, 2-hydroxy-4-N-octoxybenzophenone, 4-isopropyl dibenzoyl methane, butylmethoxy dibenzoyl methane, 2-ethylhexyl 4-(3,4-dimethoxyphenylmethylene)-2,5-dioxo-1-imidazolidine propionate, octyltriazone, dimethoxycinnamic acid isooctanoic acid glyceride, polymer derivatives and silane derivatives thereof, and the like.

Furthermore, it is possible to use those in which an organic ultraviolet absorber is encapsulated in a polymer powder. The polymer powder may be or may not be hollow and the primary particle size may be in the range of 0.1 to 50 μm and the grain distribution may be broad or sharp. Examples of the polymers include an acrylic resin, methacrylic resin, styrene resin, urethane resin, polyethylene, polypropylene, polyethylene terephthalate, silicone resin, nylon, acrylamide resin. Powders in which an organic ultraviolet absorber in the range of 0.1 to 30% by weight based on the powder weight is contained are preferable, particularly it is preferable to blend 4-tert-butyl-4'-methoxydibenzoylmethane which is an UVA absorber. Note that these powders are considered as a part of the above-mentioned water-repellent resin powder if they are water-repellent and their particle size fall under the range of the particle size.

Examples of the preservatives include alkyl paraoxybenzoate, benzoic acid, sodium benzoate, sorbic acid, potassium sorbate and phenoxyethanol, while examples of the antibacterial agents include benzoic acid, salicylic acid, carbolic acid, sorbic acid, alkyl paraoxybenzoate, parachlorometacresol, hexachlorophene, benzalkonium chloride, chlorohexidine chloride, trichlorocarbanilide, triclosan, photosensitive elements and phenoxyethanol.

Examples of the thickeners and the resins include silicone compounds such as cationized silicone resin and silicone gel (includes KSG series manufactured by Shin-Etsu Chemical Co., Ltd. or the like), vegetable based polymers such as gum Arabic, gum tragacanth, arabinogalactan, locust bean gum (carob gum), guar gum, Karaya gum, carrageenan, pectin, agar, quin seed (quince), starch (rice, corn, potato, wheat) and algaecolloid, bacteria based polymers such as xanthane gum, dextran, succinogulcan, pullulan and pullulan silicone, animal based polymers such as collagen, casein, albumin and gelatin, starch based polymers such as carboxymethyl starch and methylhydroxypropyl starch, cellulose based polymers such as methyl cellulose, ethyl cellulose, methyl hydroxypropyl cellulose, carboxymethyl cellulose, hydroxymethyl cellulose, hydroxypropyl cellulose, nitrocellulose, cellulose sodium sulfate, sodium carboxymethyl cellulose, crystalline cellulose and cellulose powder, alginic acid based polymers such as sodium alginate and propylene glycol alginate, vinyl polymers such as polyvinyl methyl ether and carboxyvinyl polymer, polyoxyethylene based polymer, polyoxyethylene polyoxypropylene copolymer based polymer, acryl based polymers such as sodium polyacrylate, polyethyl acrylate and polyacrylic acid amide, polyethyleneimine, cationic polymer, inorganic based water-soluble polymers such as bentonite, magnesium aluminum silicate, laponite, hectorite and silicic anhydride, polyethylene glycol, polyvinylpyrrolidone, and the like.

Various types of physiologically active components are preferably formulated in the cosmetic composition of the present invention. The physiologically active component used in the present invention indicates a substance which induces some physiological reaction to skin when it is applied to the skin. Examples of the physiologically active components include whitening components, anti-inflammatory agents, aging preventives, slimming agents, tonic agents, antioxidants (radical scavenger), humectants, circulation promoters, drying agents, cooling agents, warming agents, vitamins, amino acids, wound healing promoters, irritation relaxants, analgesics, cell activators, skin colorants and enzyme components. Among these, natural plant extracts, seaweed extracts and herbal drug extracts are particularly preferable. In the cosmetic composition of the present invention, it is preferable to formulate one type or two or more types of these physiologically active components.

Examples of these physiologically active components include *angelica* extract, acerola extract, avocado extract, *hydrangea* extract, *althea* extract, *arnica* extract, *aloe* extract, apricot extract, apricot kernel extract, *ginkgo biloba* extract, fennel extract, turmeric extract, oolong tea extract, rose fruit extract, *echinacea* leaf extract, *scutellaria* root extract, *phellodendron* bark extract, Japanese *coptis* extract, barley extract, *hypericum* extract, white nettle extract, watercress extract, orange extract, sea water dry matter, seaweed extract, hydrolyzed elastin, hydrolyzed wheat powder, hydrolyzed silk, chamomile extract, carrot extract, *artemisia capillaris* extract, *glycyrrhiza* extract, *hibiscus sabdariffa* extract, *pyracantha fortuneana* fruit extract, kiwi extract, *cinchona* extract, cucumber extract, guanosine, *gardenia* extract, *sasa albomarginata* extract, *sophora* root extract, cranberry extract, walnut extract, grapefruit extract, *clematis* extract, *chlorella* extract, mulberry bark extract, gentian extract, black tea extract, yeast extract, burdock root extract, rice bran fermentation extract, rice germ oil, comfrey extract, collagen, *vaccinium vitis-idaea* extract, *asiasarum* root extract, *bupleurum* root extract, umbilical cord extract, *salvia* extract, *saponaria* extract, *sasa*-bamboo extract, *crataegus* fruit extract, *zanthoxylum* fruit extract, *shiitake* extract, *rehmannia* root extract, *lithospermum* root extract, *perilla* extract, tiliaceae extract, *filipendula* extract, peony root extract, *acorus calamus* root extract, birch bark extract, horsetail extract, ivy extract, hawthorn extract, *sambucus* extract, yarrow extract, peppermint extract, sage extract, mallow extract, *cnidium* rhizome extract, *swertia* herb extract, soy bean extract, jujube extract, wild thyme extract, green tea extract, clove extract, *Imperata* cylindrical extract, *citrus unshiu* peel extract, Japanese *angelica* root extract, *calendula* extract, peach kernel extract, bitter orange peel extract, *houttuynia* extract, tomato extract, natto extract, *ginseng* extract, garlic extract, wild rose extract, *hibiscus* extract, *ophiopogon* tuber extract, parsley extract, honey, witch hazel extract, *parietaria* extract, *isodonis herba* extract, loquat extract, coltsfoot extract, *petasites japonicus* extract, hoelen extract, butcherbroom extract, grape extract, *propolis*, sponge gourd extract, safflower extract, linden extract, *paeonia* extract, hops extract, pine tree extract, horse chestnut extract, *lysichiton camtschatcense* extract, *mukurossi* peel extract, balm mint extract, peach extract, cornflower extract, *eucalyptus* extract, saxifrage extract, *citrus junos* extract, *coix* seed extract, mugwort extract, lavender extract, apple extract, lettuce extract, lemon extract, Chinese milk vetch extract, rose extract, rosemary extract, Roman chamomile extract and royal jelly extract.

In addition, biopolymers such as deoxyribonucleic acid, mucopolysaccharide, sodium hyaluronate, sodium chondroitin sulfate, collagen, elastin, chitin, chitosan and hydrolyzed shell membrane, amino acid derivatives such as amino acid, sarcosine and N-methyl-L-serine, moisturizing components such as sodium lactate, urea, sodium pyrrolidone carboxylate, betaine, whey and raffinose, oily components such as sphingolipid, ceramide, cholesterol, cholesterol derivative and phospholipid, anti-inflammatory agents such as $\epsilon$-aminocaproic acid, glycyrrhizinic acid, $\beta$-glycyrrhetinic acid, lysozyme chloride, guaiazulene and hydrocortisone, vitamins such as vitamin A, B2, B6, C, D, E, calcium pantothenate, biotin, nicotinic acid amide and vitamin C ester, active ingredients such as allantoin, diisopropylamine dichloroacetic acid, $\gamma$-aminobutyric acid, $\gamma$-amino-$\beta$-hydroxybutyric acid and 4-aminomethyl cyclohexanecarboxylic acid, antioxidants such as tocopherol, carotenoid, flavonoid, tannin, lignan and saponin, cell activators such as $\alpha$-hydroxy acid and $\beta$-hydroxy acid, blood circulation accelerators such as $\gamma$-orizanol, and vitamin E derivatives, wound healing agents such as retinol and retinol derivatives, whitening agents such as arbutin, Kojic acid, placenta extract, sulfur, ellagic acid, linoleic acid, tranexamic acid and glutathione, cepharanthine, red pepper tincture, hinokitiol, iodinated garlic extract, pyridoxine hydrochloride, dl-$\alpha$-tocopherol, acetic acid dl-$\alpha$-tocopherol, nicotinic acid, nicotinic acid derivatives, calcium pantothenate, D-pantothenyl alcohol, acetyl pantothenyl ethyl ether, biotin, allantoin, isopropylmethylphenol, estradiol, ethynyl estradiol, capronium chloride, benzalkonium chloride, diphenhydramine hydrochloride, takanal, camphor, salicylic acid, vanillyl amide nonylate, vanillyl amide nonylate, Piroctone Olamine, glyceryl pentadecanoate, 1-menthol, mononitro guaiacol, resorcin, and the like.

Although dependent upon the concentration at which the effects of the active component are exhibited, the formulating ratio of these physiologically active components in the cosmetic composition is typically preferably 0.05 to 20% by weight, and more preferably 0.1 to 15% by weight based on the total amount of the cosmetic composition. Furthermore, it is preferable to formulate one type or combine two or more types of physiologically active components.

Although there are no particular restrictions on the cosmetic composition of the present invention, preferable examples include skin care products, hair products, antiperspirants, makeup products and ultraviolet protective products. Although examples of these include milky lotion, cream, lotion, sun screen, sun tan agent, anti-acne cosmetics, essence and other basic cosmetics, foundation, whitening powder, eye shadow, eye liner, eye brow liner, cheek powder, nail color, lipstick and other makeup cosmetics, rinse, conditioner, hair color, setting agent, hair restorer, deodorant and perfume. Among of these, it is particularly preferable to apply to the sun screen, the sun tan agent, the foundation base and the foundation having the ultraviolet ray protective effects. In addition, although there are no particular restrictions on product form, the present invention can be applied to liquids, milky lotions, creams, solids, pastes, gels, powders, multi-layered forms, mousses and sprays, and particularly the liquid multi-layer separation type preparation is preferable.

EXAMPLE

The following provides a detailed explanation of the present invention through its examples and comparative examples. In addition, methods for evaluating the various characteristics of cosmetic composition used in the examples and comparative examples are indicated below.

[Evaluation of Water-Runability]

The water-runability of samples were evaluated by the above-mentioned test method using a glass plate. Regarding the case where water-runability was recognized, temperature dependency (comparison of water-runability at 25, 30, 35° C.) was also examined. The test was conducted using an amount of flowing water in the range of 50 to 150 mL/sec and the glass plate was put in and out of the running water repeatedly at an angle of 45 to 90 degree with respect to the water flow. The frequency of in and out was once per second. As the evaluation standard of water-runability, the case where water drops or water films at 30° C. flow down within 1.5 seconds was determined as "with water-runability"; the case where it exceeds 3 seconds for the water drops or the water films to flow down was determined as "with weak water water-runability"; and the case where the water films remain as they are formed or a large amount of water drops remain was determined as "with no water-runability". As the evaluation standard of the temperature dependency of water-runability, comparing the degree of water-runability at 25° C. with the degrees of water-runability at 30° C. and 35° C., the case where there is no reduction in the degree of properties was determined as "not temperature dependent"; the case where there is a slight reduction in the degree of properties was determined as "slightly temperature dependent"; and the case where there is a remarkable reduction in the degree of the properties was determined as "temperature dependent".

[Evaluation of Utilizability on Skin]

Ten expert panelists were assigned to each evaluation parameter (although some panelists were assigned to more than one parameter). Evaluations were made in accordance with the evaluation standards shown in Table 1, and the total scores of all panelists were used as evaluation results. Thus, a higher score indicates a higher degree of usefulness with respect to the evaluated parameter (maximum score: 50 points). The test was carried out at an indoor pool facility in Kanagawa prefecture and a leisure facility in Okinawa prefecture on the condition that 4 hour water bathing has been conducted.

TABLE 1

| Criterion | Score |
| --- | --- |
| Felt to be highly effective | 5 |
| Felt to be effective | 4 |
| Felt to be somewhat effective | 3 |
| Felt to only be slightly effective | 2 |
| Not felt to be effective | 1 |

Example 1

Octylsilylated fine particle titanium oxide (10% by weight of octylsilane-treated silica/alumina-treated fine particle titanium oxide. Average primary particle size: 17 nm), octylsilylated fine particle zinc oxide (10% by weight of octyltriethoxysilane-treated silica-treated fine particle zinc oxide. Average primary particle size: 45 nm), branched tetramer of methylsiloxane (volatile silicone) and silicone elastomer spherical powder (aggregate of spherical particles comprising a powder having a primary particle size of 2 to 20 μm as a main component, Trefil E-508 manufactured by Toray-Dow Corning Silicone Co.) crushed paste (the substance obtained by kneading 35 parts by weight of silicone elastomer and 65 parts by weight of cyclic silicone pentamer at a high speed using an extruder) were used and treated based on the formulation and the preparation process in Table 2 to obtain a sun screen serving also as a basic cosmetic. The unit of the formulation amount is % by weight.

TABLE 2

| Component | Formulation Amount |
|---|---|
| (Component A) | |
| Octyl paramethoxycinnamate (100 mm$^2$/s) | 10 |
| Methylphenylpolysiloxane (15 mm$^2$/s) | 4 |
| (Component B) | |
| Silicone elastomer spherical powder crushed paste | 4 |
| (Component C) | |
| Solution of trifluoropropyl-modified trimethylsiloxy silicate 50% by weight in cyclic silicone (pentamer) | 1 |
| (Component D) | |
| Decamethylcyclopentasiloxane (boiling point: 210° C.) | 26 |
| Branched tetramer of methylsiloxane (boiling point: 191° C.) | 10 |
| Ethyl alcohol | 3 |
| (Component E) | |
| Dispersion of octylsilylated fine particle titanium oxide · 50% by weight of decamethylcyclopentasiloxane | 8 |
| Octylsilylated fine particle zinc oxide | 15 |
| (Component F) | |
| Highly polymerized dimethylpolysiloxane (Degree of polymerization: 3,300) | 1 |
| (Component G) | |
| 1,3-Butylene glycol | 5 |
| Purified water | remainder |
| (Other components) | |
| Aloe extract | 0.2 |
| Preservative | q.s. |

After each component was weighed and mixed, they were filled in a light-shielding resin bottle in which a stainless ball was placed to obtain a product. When the surface shape of the coating film of this product was measured, a large number of fine asperities in which there are three or more projections, in average, having a height of 0.2 μm or more per 10 μm-length were confirmed. Furthermore, the preparation had high UV cut effect. (SPF=50+).

Comparative Example 1

Comparative example was carried out using a commercially available sun screen with high durability (SPF value>130). When the coating film of this product was examined, there were less than three projections, in average, having a height of 0.2 μm or more per 10 μm-length. Whereas the surface was relatively smooth and water-repellency was excellent, no water-runability was exhibited.

Comparative Example 2

The product was obtained in the same manner as Example 1 except that the formulation amount of methylphenylpolysiloxane of Example 1 was increased to 35% by weight, decamethylcyclopentasiloxane was changed to 5% by weight and the branched tetramer of methylsiloxane was changed to 0% by weight. (Example of the case where Component A was outside the defined range).

When the coating film of this product was examined, there were less than three projections, in average, having a height of 0.2 μm or more per 10 μm-length and the surface was relatively smooth.

Comparative Example 3

The product was obtained in the same manner as Example 1 except that the silicone elastomer spherical powder crushed paste and the solution of trifluoropropyl-modified trimethylsiloxysilicate 50% by weight in cyclic silicone (pentamer) of Example 1 were not formulated. (Example of the case where Components B and C were outside the defined range.)

When the coating film of this product was examined, there were less than three projections, in average, having a height of 0.2 μm or more per 10 μm-length and the surface was relatively smooth.

Comparative Example 4

The product was obtained in the same manner as Example 1 except that the formulation amount of the silicone elastomer spherical powder crushed paste of Example 1 was changed to 25% by weight. (Example of the case where Component B was outside the defined range.)

When the coating film of this product was examined, there were less than three projections, in average, having a height of 0.2 μm or more per 10 μm-length and the surface was relatively smooth.

Comparative Example 5

The product was obtained in the same manner as Example 1 except that the formulation amount of the solution of trifluoropropyl-modified trimethylsiloxysilicate 50% by weight in cyclic silicone (pentamer) was changed to 20% by weight. (Example of the case where Component C was outside the defined range.)

When the coating film of this product was examined, there were less than three projections, in average, having a height of 0.2 μm or more per 10 μm-length and the surface was relatively smooth.

Example 2

Silica-treated fine particle zinc oxide (average primary particle size of 30 nm, referred to as silicone-treated fine particle zinc oxide) subjected to a coating/heating treatment by 3% by weight of methylhydrogen polysiloxane (KF9901 manufactured by Shin-Etsu Chemical Co., Ltd.) as a water-repellent treated pigment; octyltriethoxysilane-treated silica/alumina-treated fine particle titanium oxide (average primary particle size of 17 nm, referred to as octylsilylated fine particle titanium oxide, using the substance finely dispersed in cyclic silicone using a bead mill); octyltriethoxysilane-treated iron oxide (yellow iron oxide, red iron oxide, black iron oxide); and silica-treated pigment grade titanium oxide (average primary particle size of 0.3 μm) (referred to as octylsilylated pigment), and as for silicone elastomer spherical powder crushed paste, the same one as in Example 1, were used. The material was treated based on the prescription in Table 3 to obtain a foundation. The unit of the formulation amount was % by weight.

TABLE 3

| Component | formulation Amount |
|---|---|
| (Component A) | |
| Octyl paramethoxycinnamate (100 mm$^2$/s) | 10 |
| Methylphenylpolysiloxane (15 mm$^2$/s) | 6 |
| Dimethylpolysiloxane (20 mm$^2$/s) | 1 |
| Dimethylpolysiloxane (1000 mm$^2$/s) | 0.3 |
| (Component B) | |
| Silicone elastomer spherical powder crushed paste | 6 |
| Polymethylsilsesquioxane (Tospal 145A manufactured by GE Toshiba Silicone Co., primary particle size of 4.5 μm) | 0.5 |
| (Component C) | |
| Solution of trifluoropropyl-modified trimethylsiloxysilicate 50% by weight in cyclic silicone (pentamer) | 1 |
| (Component D) | |
| Decamethylcyclopentasiloxane | 28 |
| Branched tetramer of methylsiloxane | 10 |
| (Component E) | |
| Silicone-treated fine particle zinc oxide | 7 |
| Dispersion of octylsilylated fine particle titanium oxide · 50% by weight of decamethylcyclopentasiloxane | 8 |
| Octylsilylated iron oxide | 0.4 |
| Octylsilylated titanium oxide | 8 |
| (Component G) | |
| Dipropylene glycol | 3 |
| Purified water | remainder |
| (Other components) | |
| Cranberry extract | 0.3 |
| Preservative | q.s. |

Component E except for the dispersion of octylsilylated fine particle titanium oxide-50% by weight of decamethylcyclopentasiloxane was mixed with a mixer. Then, after weighing and adding Components A, B and C, the dispersion of octylsilylated fine particle titanium oxide·50% by weight of decamethylcyclopentasiloxane and Component E were added and sufficiently mixed and further sufficiently mixed. The thus obtained solution was filled in a light-shielding resin bottle in which a stainless ball was placed to obtain a product.

When the surface shape of the coating film of this product was measured, a large number of fine asperities in which there are three or more projections, in average, having a height of 0.2 μm or more per 10 μm-length were confirmed. Further, the preparation had high UV cut effect. (SPF=50+).

Comparative Example 6

Commercially available W/O emulsion type lasting foundation (product featuring properties of high durability, waterproof and oil-proof) was used as a comparative example.

When the coating film of this product was examined, there were less than three projections, in average, having a height of 0.2 μm or more per 10 μm-length and the surface was relatively smooth.

Example 3

As water-repellent treated pigments, zinc oxide microparticle treated by 12% by weight of octyltriethoxysilane based on the paritcles (average primary particle size of 30 nm, referred to as octylsilylated fine particle zinc oxide) and a silicone elastomer spherical powder crushed paste, the same substances as in Example 1 were used and according to the prescription in Table 4, a transparent and favorable-feeling sun screen was obtained. The unit of the formulation was % by weight.

TABLE 4

| Component | formulation Amount |
|---|---|
| (Component A) | |
| Octyl paramethoxycinnamate (100 mm$^2$/s) | 10 |
| Methylphenylpolysiloxane (15 mm$^2$/s) | 3 |
| (Component B) | |
| Silicone elastomer spherical powder crushed paste | 3 |
| (Component C) | |
| Trifluoropropyl-modified trimethylsiloxysilicate 50% by weight cyclic silicone (pentamer) solution | 2 |
| (Component D) | |
| Decamethylcyclopentasiloxane | 13.4 |
| Branched tetramer of methylsiloxane | 15.3 |
| Ethyl alcohol | 1 |
| (Component E) | |
| Dispersion of octylsilylated fine particle zinc oxide · (mixture of 50% by weight of decamethylcyclopentasiloxane and 5% branched tetramer of methylsiloxane) | 33.3 |
| (Component F) | |
| Highly polymerized dimethylpolysiloxane (degree of polymerization: 3,300) | 1 |
| (Component G) | |
| 1,3-Butylene glycol | 3 |
| Purified water | reminder |
| (Other components) | |
| Aloe extract | 0.1 |
| Acerola extract | 0.1 |
| loquat extract | 0.1 |
| Cranberry extract | 0.1 |
| Preservative | q.s. |

After each component was weighed and mixed, they were filled in a light-shielding resin bottle in which a stainless ball was placed to obtain a product. When the surface shape of the coating film of this product was measured, a large number of fine asperities in which there are three or more projections, in average, having a height of 0.2 μm or more per 10 μm-length were confirmed. Further, the preparation had high UV cut effect. (SPF=50+).

Example 4

The sun screen was obtained in the same manner as Example 3 using a conventional method except that 1% by weight of sorbitan mono-isostearate was further added to the prescription of Example 3 as a surfactant. When the surface shape of the coating film of this product was measured, there were three or more projections, in average, having a height of 0.2 μm or more per 10 μm-length.

Comparative Example 7

The product was obtained in the same manner as Example 3 except that dimethylpolysiloxane (3000 mm²/S) (13% by weight in total) was used instead of Component A of Example 3, i.e., octyl paramethoxycinnamate (100 mm²/S) and methylphenylpolysiloxane (15 mm²/S). (in the case where a component having a viscosity outside of the viscosity range of component A).

When the coating film of this product was examined, there were less than three projections, in average, having a height of 0.2 μm or more per 10 μm-length and the surface was relatively smooth.

The results of evaluations regarding each Example and Comparative example were shown in the following Tables 5 and 6. The presence of water-runability was examined by a test using the above-mentioned glass plate, and as for the remaining evaluation items, field tests were conducted.

TABLE 5

|  | Water-runability | Temperature dependency of water-runability |
| --- | --- | --- |
| Example 1 | Present | Not present |
| Comparative Example 1 | Not present | — |
| Comparative Example 2 | Weak | — |
| Comparative Example 3 | Weak | Present |
| Comparative Example 4 | Weak | Present |
| Comparative Example 5 | Present | Present |
| Example 2 | Present | Not present |
| Comparative Example 6 | Not present | — |
| Example 3 | Present | Not present |
| Example 4 | Present | Slightly present |
| Comparative Example 7 | Not present | — |

TABLE 6

|  | Lastingness of water-proof properties | Water easily flows down from the skin | Excellent in feeling |
| --- | --- | --- | --- |
| Example 1 | 50 | 50 | 46 |
| Comparative Example 1 | 31 | 16 | 33 |
| Comparative Example 2 | 23 | 38 | 10 |
| Comparative Example 3 | 29 | 37 | 42 |
| Comparative Example 4 | 25 | 34 | 36 |
| Comparative Example 5 | 50 | 50 | 10 |
| Example 2 | 46 | 46 | 39 |
| Comparative Example 6 | 10 | 10 | 44 |
| Example 3 | 49 | 50 | 50 |
| Example 4 | 45 | 44 | 48 |
| Comparative Example 7 | 18 | 13 | 10 |

The results in Tables 5 and 6 show that Examples of the present invention have excellent performance with good balance with regard to each item of water-runability, lastingness of water-proof properties and feeling as compared with their respective Comparative examples. In contrast, Comparative examples 1 and 6 are examples using commercially available products and it is understood that no water-runability was recognized, and even if the durability under conventional criteria was excellent, the durability was relatively inferior when the preparations of the present invention were used as a reference. Further, Comparative example 2 is an example of the case where Component A was increased to the outside of the defined range and it is understood that although weak water-runability was obtained, the oily feeling was so strong that the feeling was not good. Comparative example 3 is an example of the case where Components B and C were not formulated, water-runability was weak and the lastingness of the properties was also weak. Comparative example 4 is an example of the case where Component B was increased to the outside of the defined range and it is understood that water-runability was weak and there was a problem with durability. Comparative example 5 is an example of the case where Component C was increased to the outside of the defined range and there was a problem that although water-runability and durability are excellent, the feeling was bad and the product could not be taken off with a conventional cleansing agent. In Example 2, make-up effect was maintained even during water bathing. On the other hand, in Comparative example 6, the cosmetic composition was removed during water bathing and the make-up effect has disappeared. Comparative example 7 is an example of the case where a non-volatile oil agent having a high viscosity was formulated, the product became water-repellent, water-runability was not exhibited, and the water-repellent coating film became blended with water over time (1 hour). Although the examples of the present invention had water-runability, the washing became possible by a conventional cleansing agent. Further, Examples 1 to 3 had no temperature dependency as compared with Comparative examples and the stable water-runability was exhibited even at a low temperature (25° C.). Example 4 is an example where the surfactant was formulated and although water-runability was exhibited, temperature dependency of the water-runability slightly appeared.

INDUSTRIAL APPLICABILITY

As mentioned above, the cosmetic composition of the present invention contains the following Components (A) to (E):

(A) 7 to 30% by weight of one or more kinds of non-volatile oil agents having a kinematic viscosity of 5 to 1000 mm²/s at 25° C.;
(B) 0.2 to 5% by weight of one or more kinds of water-repellent resin powders whose primary particle size is in the range of 2 to 20 μm;
(C) 0.1 to 6% by weight of one or more kinds of oil-soluble silicone resins;
(D) 20 to 60% by weight of volatile solvent containing one or more kinds of volatile solvent whose boiling point at 1 atmosphere is 200° C. or lower except for water; and
(E) 12 to 30% by weight of one or more kinds of water-repellent surface treated pigments, the water-runability is stable without showing temperature dependency, excellent in durability and feeling, and UV protective effects are excellent. The cosmetic composition is preferred as a skin care product, a hair care product, an antiperspirant product, a make-up product, a UV protective product and the like.

What is claimed is:
1. A cosmetic composition which comprises the following Components (A) to (E)
(A) 7 to 30% by weight of one or more non-volatile oil agents having a kinematic viscosity of 5 to 1000 mm²/s at 25° C., wherein the non-volatile oil agent is selected from the group consisting of dimethylpolysiloxane, methylphenylpolysiloxane, and octyl paramethoxycinnamate;

(B) 0.2 to 5% by weight of one or more water-repellent resin powders whose particle size of the primary particle is in the range of 2 to 20 μm, wherein the water-repellent resin powder is selected from an organopolysiloxane elastomer spherical powder, a silicone resin-treated organopolysiloxane elastomer spherical powder, polymethylsilsesquioxane and polyalkylsilsesquioxane;

(C) 0.1 to 6% by weight of one or more oil-soluble silicone resins selected from the group consisting of perfluoroalkyl group-containing polyalkylsiloxysilicate;

(D) 20 to 60% by weight of one or more volatile solvents, excluding water, selected from the group consisting of cyclic tetra- to hexamer of dimethylpolysiloxane, branched tetramer of dimethylpolysiloxane (methyl trimethicone), linear dimethylpolysiloxane and a lower alcohol;

wherein the volatile solvent(s) contains (contain) at least one volatile solvent whose boiling point at 1 atmosphere is 200° C. or lower;

(E) 12 to 30% by weight of one or more water-repellent surface treated pigments, wherein the water-repellent surface treated pigment is selected from pigments subjected to silane treatment with organosilane having an alkyl group with carbon numbers of 6 to 20 which may be substituted and pigment subjected to silicone treatment; and (F) a highly polymerized silicone represented by the following general formula:

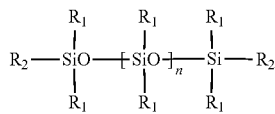

wherein R1 represents a methyl group or a phenyl group, and R2 represents a methyl group or a hydroxyl group, provided that the case where all of R1 are phenyl groups is excluded, n represents an integer of 2,000 to 20,000.

2. The cosmetic according to claim 1, containing no surfactant other than a surfactant selected from the group consisting of perfluoroalkyl-modified silicone, polyether modified silicone, polyglyceryl-modified silicone, alkylpolyglyceryl-modified silicone and perfluoroalkyl polyether-comodified silicone.

3. The cosmetic composition according to claim 1, further comprising as Component (G) water and/or polyhydric alcohols.

4. The cosmetic composition according to claim 1, wherein the water-repellent resin powder is formulated in a form of being kneaded with an oil agent, finely crushed by a crusher or dispersed in water.

5. The cosmetic composition according to claim 1, wherein at least one or more of the water-repellent surface treated pigment is selected from the group consisting of a fine particle titanium oxide with an average primary particle size of 1 to 100 nm, a fine particle zinc oxide with an average primary particle size of 1 to 100 nm, a fine particle cerium oxide with an average primary particle size of 1 to 100 nm, a fine particle iron-doped titanium oxide with an average primary particle size of 1 to 200 nm, a fine particle silicic anhydride with an average primary particle size of 1 to 100 nm, a fine particle alumina with an average primary particle size of 1 to 100 nm and a fine particle zirconia with an average primary particle size of 1 to 100 nm.

6. The cosmetic composition according to claim 1, wherein the water-repellent surface treated pigment is coated with silica, alumina or zirconia, and further subjected to water-repellent surface treatment.

7. The cosmetic composition according to claim 1, wherein one or more of the water-repellent surface treated pigments is formulated in a solvent or an oil agent in a mechanically ground form in advance or at the time of production of the cosmetic product.

8. The cosmetic composition according to claim 1, wherein the water-repellent surface treatment is octylsilane treatment.

9. The cosmetic composition according to claim 1, wherein when 10 mg of the cosmetic composition is applied to and uniformly spread on one side of a 5×10 cm flat and smooth glass plate, dried at 32° C. for 5 minutes, then repeatedly put in and out of running water at 30° C. for two minutes, then immersed completely in the water, slanted at an angle of 30 degree with respect to the water surface and rapidly pulled out of the water, the cosmetic composition shows water-runability such that water drops or water films fall down from the glass surface within three seconds.

10. The cosmetic composition according to claim 1, wherein when 10 mg of the cosmetic composition is applied to and uniformly spread on one side of a 5×10 cm flat and smooth glass plate, dried at 32° C. for 5 minutes, then repeatedly put in and out of running water at 30° C. for two minutes, then dried at 50° C. for 1 hour, the coated portion on the glass plate has three or more of protruding portions having a height of 0.2 μm or more per 10 μm-length.

11. A method of imparting water-runability on skin or hair by applying or spraying the cosmetic composition as set forth in claim 1 on the skin or the hair.

12. A method of imparting water-runability on skin or hair by applying or spraying the cosmetic composition as set forth in claim 4 on the skin or the hair.

13. A method of imparting water-runability on skin or hair by applying or spraying the cosmetic composition as set forth in claim 5 on the skin or the hair.

14. A method of imparting water-runability on skin or hair by applying or spraying the cosmetic composition as set forth in claim 10 on the skin or the hair.

* * * * *